United States Patent
Kim et al.

(10) Patent No.: US 12,421,267 B2
(45) Date of Patent: Sep. 23, 2025

(54) COMPOSITION FOR PREPARING ALLULOSE AND METHOD FOR PREPARING ALLULOSE BY USING SAME

(71) Applicant: CJ CHEILJEDANG CORPORATION, Seoul (KR)

(72) Inventors: Minhoe Kim, Seoul (KR); Sungkyun Lee, Seoul (KR); Taekbeom Kim, Seoul (KR); Youn Kyung Bak, Seoul (KR); Seong Bo Kim, Seoul (KR); Eun Jung Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 678 days.

(21) Appl. No.: 17/779,043

(22) PCT Filed: Nov. 23, 2020

(86) PCT No.: PCT/KR2020/016551
§ 371 (c)(1),
(2) Date: May 23, 2022

(87) PCT Pub. No.: WO2021/107522
PCT Pub. Date: Jun. 3, 2021

(65) Prior Publication Data
US 2023/0002434 A1  Jan. 5, 2023

(30) Foreign Application Priority Data

Nov. 29, 2019 (KR) .................. 10-2019-0156761

(51) Int. Cl.
*C07H 1/00* (2006.01)
*C07H 3/02* (2006.01)

(52) U.S. Cl.
CPC .................. *C07H 1/00* (2013.01); *C07H 3/02* (2013.01)

(58) Field of Classification Search
None
See application file for complete search history.

(56) References Cited

U.S. PATENT DOCUMENTS

| 11,084,805 | B2 * | 8/2021 | Kim ................. C07H 3/04 |
| 2018/0049458 | A1 | 2/2018 | Woodyer et al. |
| 2018/0327796 | A1 | 11/2018 | Lee et al. |
| 2019/0328014 | A1 * | 10/2019 | Boit ................. B01D 61/04 |
| 2023/0002434 | A1 | 1/2023 | Kim et al. |

FOREIGN PATENT DOCUMENTS

| CN | 1528916 A | 9/2004 | |
| CN | 111989337 A | 11/2020 | |
| CO | 2022009062 A1 | 7/2022 | |
| EP | 4 046 498 A1 | 8/2022 | |
| JP | 10-234359 A | 9/1998 | |
| JP | 2005-110675 A | 4/2005 | |
| JP | 2010-124824 A | 6/2010 | |
| JP | 2011-037821 A | 2/2011 | |
| JP | 2011-062196 A | 3/2011 | |
| KR | 10-2016-0041380 A | 4/2016 | |
| KR | 10-2019-0049499 A | 5/2019 | |
| KR | 10-2019-0100222 A | 8/2019 | |
| KR | 10-2019-0101389 A | 8/2019 | |
| WO | 2012/113405 A1 | 8/2012 | |
| WO | WO-2018127669 A1 * | 7/2018 | ............. A23L 27/33 |
| WO | 2019/156483 A1 | 8/2019 | |

OTHER PUBLICATIONS

Abraham et al., "Toxicology and risk assessment of 5-Hydroxymethylfurfural in food," *Mol. Nutr. Food Res.* 55:667-678 (2011).
Friedman, "Food Browning and Its Prevention: An Overview," *J. Agric. Food Chem.* 44(3):631-653 (1996).
Kowalski et al., "5-Hydroxymethyl-2-Furfural (HMF)—Heat-Induced Formation, Occurrence in Food and Biotransformation—a Review," *Pol. J. Food Nutr. Sci.* 63(4):207-225 (2013).
Morimoto et al., "Production and application of a rare disaccharide using sucrose phosphorylase from *Leuconostoc mesenteroides*," *Journal of Bioscience and Bioengineering* 119(6):652-656 (2015).
Oshima et al., "Synthesis and Structure Analysis of Novel Disaccharides Containing D-Psicose Produced by Endo-1,4-β-D-Xylanase from *Aspergillus sojae*," *Journal of Bioscience and Bioengineering* 101(3):280-283 (2006).
Stack Exchange, What types of glycosidic bonds are in the oligosaccharides that occurs naturally not in the lab?, Chemistry, Jan. 7, 2017, URL=https://chemistry.stackexchange.com/questions/65832/what-types-of-glycosidic-bonds-are-in-oligosaccharides-that-occurs-naturally-not. (2 pages).
Vollhardt et al., "24.1: Names and Structures of Carbohydrates," LibreTexts Textmap, 2 Organic Chemistry, Jan. 1, 2014. (20 pages).

* cited by examiner

*Primary Examiner* — Traviss C McIntosh, III
(74) *Attorney, Agent, or Firm* — Seed Intellectual Property Law Group LLP

(57) ABSTRACT

Provided are a novel composition for preparing allulose and a method of preparing allulose using the same.

6 Claims, 4 Drawing Sheets

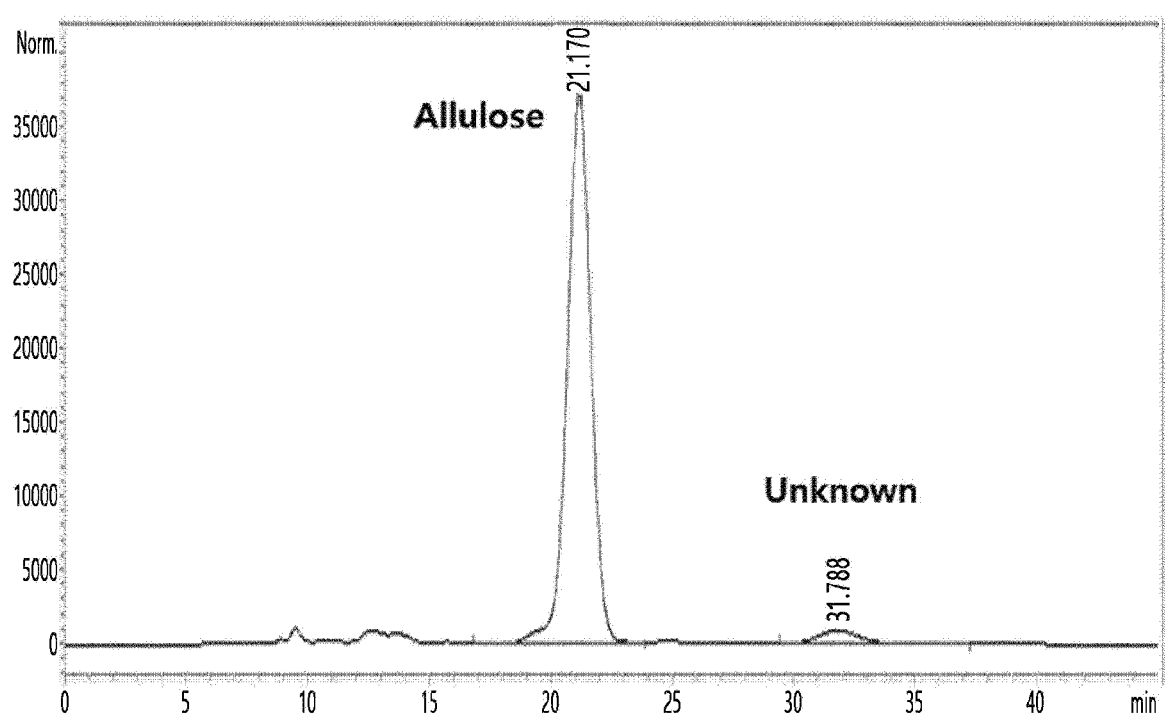
[FIG. 1]

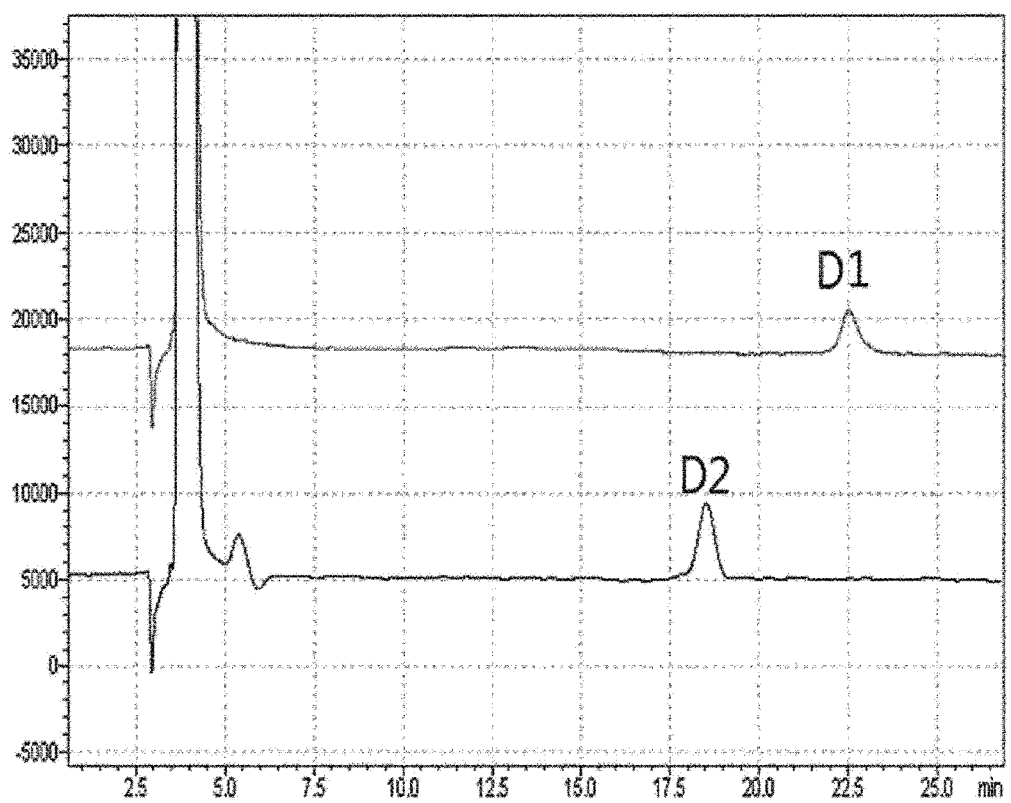
[FIG. 2]

[FIG. 3]
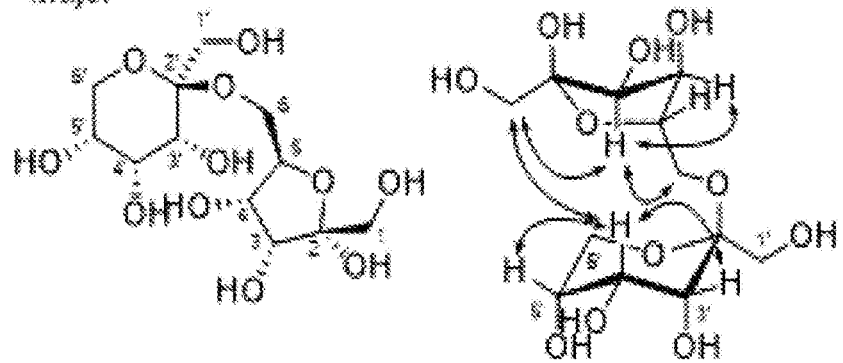
6-O-β-D-Psicopyranosyl-α-D-psicofuranose
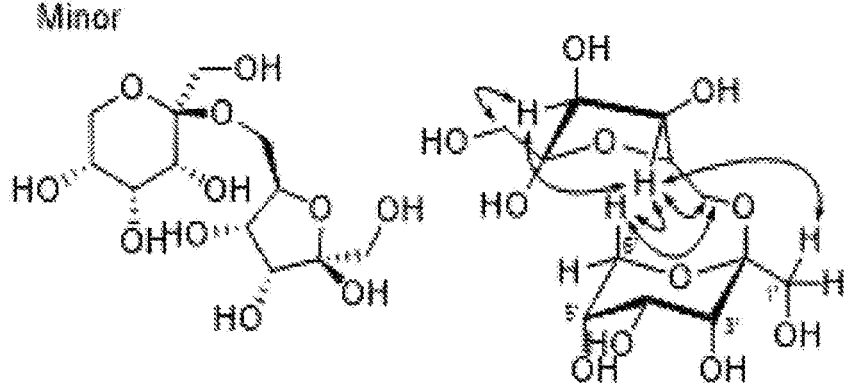
6-O-β-D-Psicopyranosyl-β-D-psicofuranose

[FIG. 4]
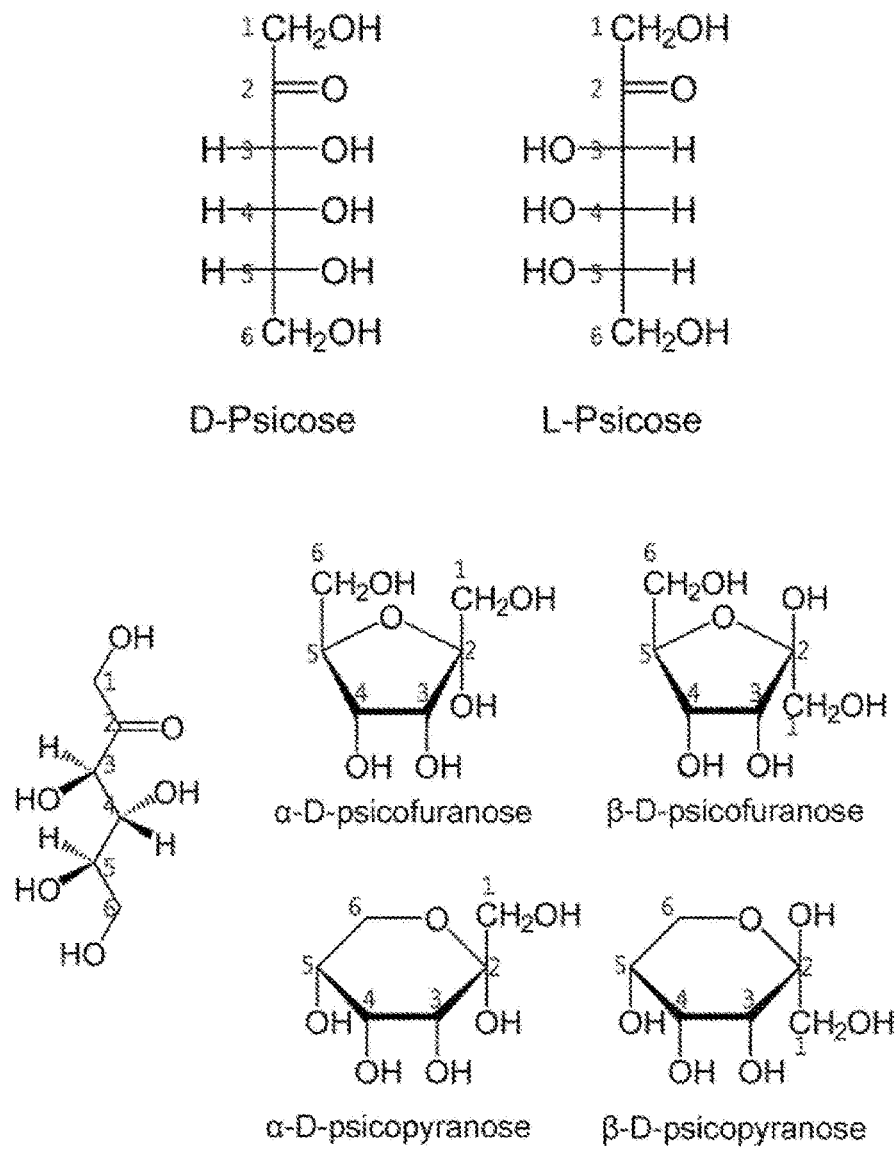

COMPOSITION FOR PREPARING ALLULOSE AND METHOD FOR PREPARING ALLULOSE BY USING SAME

BACKGROUND OF THE INVENTION

1. Field of the Invention

The present disclosure relates to a composition for preparing allulose and a method of using the same.

2. Description of the Related Art

For stable storage and distribution of saccharides, studies have been conducted on the development (utilization) of precursors for the preparation of saccharides. For example, International Patent Publication No. WO 2012-113405 A1 discloses a precursor composition for preparing human milk oligosaccharide components with high purity, which are difficult to synthesize or purify by way of a chemical or enzymatic method. However, there are no studies on a precursor composition for preparing allulose, which is a material that has recently received attention as a low-calorie saccharide.

In view of this technical background, the present inventors have found that a novel compound may be used as a precursor for preparing allulose, thereby completing the present disclosure.

SUMMARY OF THE INVENTION

An object of the present disclosure is to provide a novel composition for preparing allulose, and a method of preparing allulose using the same.

BRIEF DESCRIPTION OF THE DRAWINGS

FIG. 1 shows an HPLC chromatogram of a disaccharide generated during a process of preparing allulose, as analyzed by a size exclusion column (Biorad Aminex HPX-87C);

FIG. 2 shows an HPLC chromatogram of D1 and D2, which are in a mixture form, obtained by the size exclusion column from the disaccharide generated during the process of preparing allulose, as analyzed by a normal phase column (YMC Pack Polyamine H);

FIG. 3 shows a stereoscopic structure of D1, which is an allulose disaccharide; and FIG. 4 shows structures of allulose and numbered carbon atoms thereof.

DETAILED DESCRIPTION OF THE PREFERRED EMBODIMENTS

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

Further, those skilled in the art will recognize, or be able to ascertain using no more than routine experimentation, many equivalents to the specific embodiments of the disclosure described herein. Further, these equivalents should be interpreted to fall within the present disclosure.

An aspect of the present disclosure provides a novel allulose precursor.

The allulose precursor of the present disclosure may include an allulose disaccharide. The allulose precursor of the present disclosure may have a structure of the allulose disaccharide.

The "allulose disaccharide" of the present disclosure refers to a "compound, in which two allulose molecules are linked by a glycosidic bond". The term "allulose disaccharide" may be called "allulose dimer" or "disaccharide allulose".

Specifically, the allulose disaccharide may be a compound, in which two allulose molecules are linked by a glycosidic bond, the glycosidic bond linking a hydroxyl group at C2 position of one allulose molecule of the two allulose molecules to a hydroxyl group at any one position of C1 to C6 positions of the other allulose molecule.

Specifically, the allulose disaccharide may be a compound, in which at least one molecule of two allulose molecules is a cyclic allulose, wherein a hydroxyl group at C2 position of the cyclic allulose is linked to a hydroxyl group at any one position of C1 to C6 positions of the other allulose molecule by a glycosidic bond. The glycosidic bond may be one glycosidic bond to two glycosidic bonds, and specifically one glycosidic bond.

In one embodiment, the glycosidic bond may be a glycosidic bond between the hydroxyl group at C2 position of the cyclic allulose and the hydroxyl group at C6 position of the other allulose.

In one embodiment, in the allulose precursor, one molecule of the two allulose molecules is in the form of psicofuranose and the other molecule is in the form of psicopyranose. In one embodiment, the allulose precursor may be a compound represented by the following Formula 1.

[Formula 1]

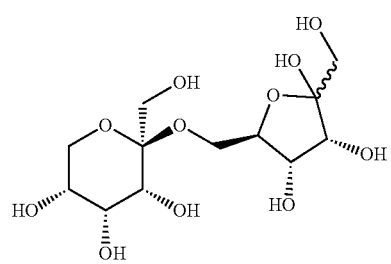

In one embodiment, the allulose precursor of the present disclosure may be a compound named 2-(hydroxymethyl)-2-(3,4,5-trihydroxy-5-(hydroxymethyl)tetranydrofuran-2,11)methoxy)tetrahydro-2H-pyran-3,4,5-trial, more specifically a compound named (2S,3R,4R,5R)-2-(hydroxymethyl)-2-(((2R,3S,4R)-3,4,5-trihydroxy-5-(hydroxymethyptetranydrofuran-2-yl)methoxy)tetrahydro-2H-pyran-3,4,5-triol, but is not limited thereto.

The (2S,3R,4R,5R)-2-(hydroxymethyl)-2-(((2R,3S,4R)-3,4,5-trihydroxy-5-(hydroxymethyl)tetranydrofuran-2,11) methoxy)tetrahydro-2H-pyran-3,4,5-trial may collectively refer to compounds named 6-O-β-D-psicopyranosyl-α-D-psica furanose 6-O-β-D-psicopyranosyl-β-D-psicofuranose, according to the form of psicofuranose.

The (2S,3R,4R,5R)-2-(hydroxymethyl)-2-(((2R,3S,4R)-3,4,5-trihydroxy-5-(hydroxymethylytetrahydrofuran-2-yl) methoxy)tetrahydro-2H-pyran-3,4,5-triol may be a compound named (2S,3R,4R,5R)-2-(hydroxymethyl)-2-(((2R, 3S,4R,5S)-3,4,5-trihydroxy-5-(hydroxymethyl)
tetrahydrofuran-2-yl)methoxy)tetrahydro-2H pyran-3,4,5-
triol, or a compound named (2S,3R,4R,5R)-2-
(hydroxyrnethyl)-2-2R,3S,4R,5R)-3,4,5-trihydroxy-5-
(hydroxymethyl)tetranydrofuran-2-yl)methoxy)tetrahydro-
2H-pyran-3,4,5-triol, but is not limited thereto.

Specifically, the compound of Formula 1 may exist in two forms of the following Formula 2 and/or Formula 3.

[Formula 2]

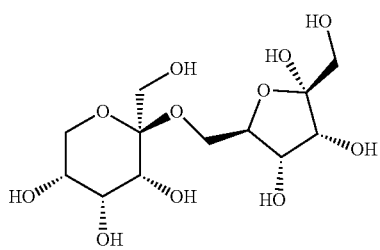

[Formula 3]

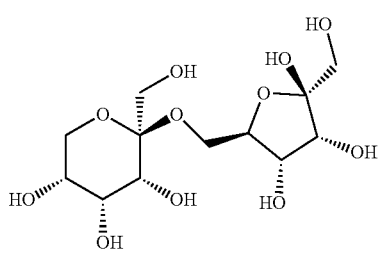

The compound of Formula 2 may be named 6-O-β-D-psicopyranosyl-α-D-psicofuranose, and the compound of Formula 3 may be named 6-O-β-D psicopyranosyl-β-D-psicofuranose.

The allulose precursor of the present disclosure may be converted to allulose by heating.

The heating may be performed at a temperature of 60° C. or higher and 100° C. or lower, and more specifically at a temperature of 60° C. or higher and 95° C. or lower, 65° C. or higher and 95° C. or lower, 70° C. or higher and 95° C. or lower, but is not limited thereto.

The heating may be performed for longer than 0 hours to 108 hours or shorter, and specifically for 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, or 12 hours or longer, but is not limited thereto.

When the allulose precursor of the present disclosure is converted to allulose, 20 parts by weight or more thereof may be converted to allulose, based on 100 parts by weight of the initial allulose precursor. Specifically, 20 parts by weight, 25 parts by weight, 30 parts by weight, 35 parts by weight, 40 parts by weight, 45 parts by weight, 50 parts by weight, 55 parts by weight, 60 parts by weight, 65 parts by weight, 70 parts by weight, 75 parts by weight, 80 parts by weight, 90 parts by weight, 95 parts by weight, or 99 parts by weight or more, or 100 parts by weight, i.e., all of the allulose precursor may be converted to allulose, based on 100 parts by weight of the initial allulose precursor, but is not limited thereto.

Meanwhile, the converting may be performed for longer than 0 hours and 108 hours or shorter, and specifically for 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, or 12 hours or longer, but is not limited thereto.

When the allulose precursor of the present disclosure, is converted to allulose, the amount of by-products produced other than the target allulose may be 10 parts by weight or less, specifically 10 parts by weight, 9 parts by weight, 8 parts by weight, 7.5 parts by weight, 7 parts by weight, 6,5 parts by, weight, 6 parts by weight, 5.5 parts by weight, 5 parts by weight, 4.5 parts by weight. 4 parts by weight, 3.5 parts by weight, 3 parts by weight, 2.5 parts by, weight, 2 parts by, weight, 1.5 parts by weight, or 1 part by weight or less, based on 100 parts by weight of the total composition, or a may be 0 parts by weight, based on 100 parts by weight of the total composition, i.e., no by-products may be generated, but is not limited thereto.

Another aspect of the present disclosure provides use of the allulose disaccharide as an allulose precursor.

Still another aspect of the present disclosure provides an allulose precursor composition including the allulose disaccharide.

Still another aspect of the present disclosure provides use of the allulose disaccharide in the preparation of allulose.

Still another aspect of the present disclosure provides a composition for preparing allulose, the composition including the allulose, disaccharide.

Still another aspect of the present disclosure provides a method of preparing allulose, the method including heating the allulose disaccharide.

As described above, the allulose disaccharide of the present disclosure may be converted to allulose, and thus the allulose disaccharide may be applied to the preparation of allulose. The allulose disaccharide, precursor, and heating are the same as described above.

Still another aspect of the present disclosure provides a method of preparing allulose, the method including heating the composition including allulose disaccharide.

As described above, the allulose disaccharide of the present disclosure may be converted to allulose, and thus the composition including the allulose disaccharide may be applied to the preparation of allulose. The allulose disaccharide, precursor, and heating are the same as described above.

The heating of the allulose disaccharide may convert the allulose disaccharide to allulose or may produce allulose, but is not limited thereto.

The composition may include saccharides. Specifically, the composition may further include allulose, but is not limited thereto.

With regard to the content of the allulose disaccharide in the composition including the allulose disaccharide, the allulose disaccharide, may be included in an amount of more than 0 parts by weight and 15 parts by weight or less, based on 100 parts by weight of the total saccharides included in the composition. Specifically, the allulose disaccharide may be included in an amount of more than 0.0001 parts by weight, more than 0.001 parts by weight, more than 0.01 parts by weight, more than 0.1 parts by weight, or more than 0.15 parts by weight, and 15 parts by weight or less, based on 100 parts by weight of the total saccharides, and/or the allulose disaccharide may be included in an amount of 15 parts by weight or less, 13 parts by weight or less, 11 parts by weight or less, 10 parts by weight or less, 9 parts by weight or less, 8 parts by weight or less, 7 parts by weight or less, 6 parts by weight or less, 5 parts by weight or less, 4 parts by weight or less, 3 parts by weight or less, 2 parts by weight or less, or 1 part by weight or less and more than 0 parts by weight, based on 100 parts by weight of the total saccharides, but is not limited thereto.

The composition may be a food composition.

The food composition includes any food without limitation, as long as allulose may be used therein. Specifically, the food composition may include general foods, health foods, and medicinal (or patient) food compositions, but is not limited thereto. Specifically, the food composition of the present disclosure may be a drink (e.g., a carbonated drink, a fruit juice drink, a fruit/vegetable drink, a dietary fiber drink, carbonated water, mixed grain powder, tea, coffee, etc.), an alcohol drink, a bakery product, a sauce (e.g., ketchup, BBQ sauce, etc.), a dairy product (e.g., fermented milk, processed milk, etc.), a processed meat (e.g., ham, sausage, beef jerky, etc.), a chocolate confectionary, a gum, a candy, a jelly, an ice cream, a syrup, a dressing, a snack (e.g., cookie, cracker, biscuit, etc.), a fruit conserve (e.g., fruit preparation, glace fruit, red ginseng juice, sliced red ginseng, etc.), a meal substitution food (e.g., a frozen food, a retort pouch, home meal replacement (HMR), etc.), or a processed food. However, this is only an example, and the food composition is not limited thereto.

The food composition of the present disclosure may include additional ingredients, such as various flavoring agents, natural carbohydrates, etc. The above-described natural carbohydrates may include monosaccharides such as glucose, fructose, and allulose, disaccharides such as maltose and sucrose, polysaccharides such as dextrin and cyclodextrin, and sugar alcohols such as xylitol, sorbitol and erythritol. As a sweetener, a natural sweetener such as thaumatin and stevia extract, a synthetic sweetener such as sucralose, saccharin, and aspartame, etc. may be used.

In addition to the ingredients described above, the food composition of the present disclosure may include various nutritional supplements, vitamins, minerals, flavors, colorants, pectin and salts thereof, alginic acid and salts thereof, organic acids, protective colloid thickeners, pH adjusters, stabilizers, preservatives, glycerin, alcohols, carbonating agents used in carbonated drinks, and the like. In addition, the food composition of the present disclosure may include flash of fruits for the preparation of natural fruit juices, fruit juice beverages, and vegetable drinks. These ingredients may be used alone or in combination thereof. The substances commonly included in the food composition may be appropriately selected and added by those skilled in the art, and a proportion of the additive may be selected from the range of 0.001 parts by weight to 1 part by weight, or 0.01 parts by weight to 0.20 parts by weight, based on 100 parts by weight of the food composition of the present disclosure, but is not limited thereto.

Still another aspect of the present disclosure provides a method of enhancing quality stability of a food, the method including heating the food composition including the allulose disaccharide.

The food may be a food including allulose.

The "enhancing quality stability" means suppressing any denaturation that may occur during distribution, storage, and processing, and consequent deterioration of quality, or lowering the level of denaturation and quality deterioration that have already occurred. Specifically, the denaturation may include a phenomenon, in which allulose is changed to a substance other than allulose or physical properties thereof are changed, such as crystallization, browning, oxidation/reduction reaction, etc.

When allulose or the composition including the same is stored for a long period of time, the food quality may deteriorate due to denaturation such as crystallization of allulose, etc. However, when the allulose precursor of the present disclosure is added to foods, allulose is obtained at a desired time by heating the allulose precursor, and thus it may be used to improve quality stability of foods.

The foods are the same as described above.

Hereinafter, the present disclosure will be described in more detail with reference to Examples and Experimental Examples. However, these Examples and Experimental Examples are for illustrative purposes only, and the scope of the present disclosure is not intended to be limited by these Examples and Experimental Examples.

EXAMPLE 1

Isolation of Allulose Precursor

A novel substance was isolated through HPLC according to an allulose preparation process disclosed in US 2018-0327796 A1.

In detail, it was confirmed that a target disaccharide ingredient was generated, and a novel (unknown) substance, in addition to allulose, was generated from a crude solution, as shown in FIG. 1, under HPLC chromatogram analysis conditions in Table 1 below. Allulose was identified at 21.1 minutes, and the novel substance was identified at 31.7 minutes.

TABLE 1

| | |
|---|---|
| Equipment | Agilent technologies 1200 series |
| Column | Biorad Aminex HPX-87C (7.8 mm × 300 mm, 9 µm) |
| Eluent | Water |
| Flow rate | 0.6 mL/min |
| Temperature | 80° C. |
| RI cell temperature | 30° C. |

In order to isolate the generated novel substance, the novel substance was precisely isolated using HPLC and a normal phase column under conditions of Table 2.

TABLE 2

| | |
|---|---|
| Equipment | Shimadzu LC 10A |
| Column | YMC Pack Polyamine II (4.6 mm × 250 mm, 5 µm, 12 nm) |
| Eluent | Acetonitrile/Water (80/20) |
| Flow rate | 1 mL/min |
| Temperature | 30° C. |
| RI cell temperature | 30° C. |

As a result, it was confirmed that the substance shown as one peak under the HPLC conditions of Table 1 was observed as two separate peaks under the separation conditions of Table 2 (FIG. 2). The substance of the peak identified at 22.5 minutes was named D1 and the other substance of the peak identified at 17.7 minutes was named D2.

D1 was further analyzed by ESI-MS $^1$H NMR, and $^{12}$C NMR.

Major 6-O-β-D-psicopyranosyl-α-D-psicofuranose was white amorphous powder, ESI-MS m/z 365 [M+Na]-f; 1H NMR (850 MHz, D$_2$O) δH 3.44 (1H, d, J 12.0 Hz), 3.47 (1H, d, J=12.0 Hz), 3.56 (1H, dd, J=11.0 Hz, 5.0 Hz), 3.60 (1H, d, J=12.0 Hz), 3.62 (1H, dd, J=11.0 Hz, 2.5 Hz), 3,70 (1H, br d, J=12.5 Hz), 3.75 (1H, d, J=12.0 Hz), 3.75 (1H, br ma), 3.82 (1H, br d, J=12.5 Hz), 3.84 (1H, br s), 3.92 (1H, t, 3.0 Hz), 3.97 (1H, d, J=5.5 Hz), 4.09 (1H, t, J=5.5 Hz), 4.13 (1H, br m) [D$_2$O signal δH 4.70]; 13C NMR signalsb δC 57.6, 60.4, 62.9, 64.7, 64.9, 69.1, 68.9, 70.2, 70.3, 81.2, 101.8, 103.4.

Minor 6-O-β-D-psicopyranosyl-β-D-psicofuranose was white amorphous powder, ESI-MS m/z 365 [M+Na]+; $^1$H NMR (850 MHz, D$_2$O) δH 3.49 (1H, d, J=13.0 Hz), 3.73 (1H, d, J=13.0 Hz), 3.58 (1H, ma), 3.68 (1H, dd, J=11.0, 2.5 Hz), 3.62 (1H, ma), 3.71 (1H, br d, J=12.0 Hz), 3.82 (1H, br d, J=12.0 Hz), 3.76 (1H, br ma), 3.78 (1H, ma), 3.87 (1H, br s), 3.98 (1H, t, J=3.0 Hz), 3.95 (1H, d, J=4.5 Hz), 4.00 (1H, br m), 4.34 (1H dd, of J=8.0 Hz, 4.5 Hz) [D$_2$O signal δH 4.70]; $^{13}$C NMR signalsb δC 57,7, 61.4, 62,2, 64.7, 64.8, 69.0, 69.2, 70.8, 74.4, 80.8, 101.8, 105.9.

As a result, it was confirmed that D1 is a novel compound in which two allulose molecules are linked, and has a structure of the following Formula 1.

[Formula 1]

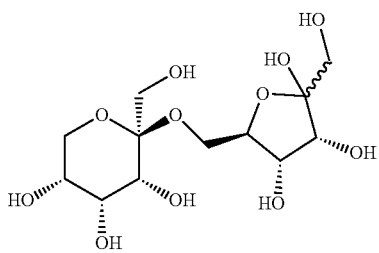

It was also confirmed that D1 has two types of major and minor forms (FIG. 3), and the major form, 6-O-β-D-psicopyranosyl-α-D-psicofuranose, has a structure of the following Formula 2, and the minor form, 6-O-β-D-psicopyranosyl-β-D-psicofuranose, has a structure of the following Formula 3.

[Formula 2]

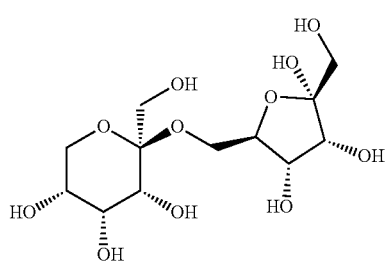

[Formula 3]

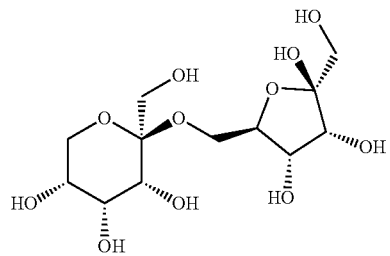

The compound of Formula 2 (6-O-β-D-psicopyranosyl-α-D-psicofuranose) was named Compound A, and the compound of Formula 3 (6-O-β-D-psicopyranosyl-β-D-psicofuranose) was named Compound B.

In addition, it was confirmed that D2 has a structural isomer relationship with the compound of Formula 1, and is a novel allulose disaccharide, in which the hydroxyl group at C2 position (according to carbon numbering of FIG. 4) of allulose is linked to the hydroxy group at any one of C1 to C6 positions of the other allulose molecule by a glycoside bond.

In the following experiments, experiments were performed in order to examine whether the novel compounds D1 and D2 may be used as allulose precursors.

EXAMPLE 2

Production of Mulose Using Allulose Precursor

EXAMPLE 2-1

Comparison of Heating Conversion Reaction of Allulose Disaccharide

Ultrapure water without impurities was added to the two types of disaccharides, D1 and D2, isolated in Example 1, to prepare samples with a concentration of 1% (w/w), which were then used in Experimental Examples 1 and 2, respectively. In order to compare decomposition reactions according to heating conditions, sugar (CJ Cheiljedang, purity of 99% or more) consisting of one molecule of glucose and one molecule of fructose, which is the most common disaccharide (dimer), was selected. In the same manner, ultrapure water was added thereto, and a sample with a concentration of 1% (w/w) was prepared, which was then used in Comparative Example 1.

Each of the prepared samples was placed in a sealed glass bottle, and heated in a water bath (DAIHAN Science) which had been preheated to 70° C., 80° C., 90° C., or 95° C. The heated samples were collected and sampled at intervals of 12 hours, and changes thereof were analyzed using HPLC under the conditions of Table, 1. All experiments were performed in triplicate, and the results are shown in Table 3 below.

TABLE 3

| Heating temperture (° C.) | Heating time (hr) | Experimental Example 1 D1, 1% | | | Experimental Example 2 D2, 1% | | | Comparative Example 1 Sugar, 1% | | |
|---|---|---|---|---|---|---|---|---|---|---|
| | | Monosaccharide (%) | Disacchadde (%) | Others (%) | Monosaccharide (%) | Disacchadde (%) | Others (%) | Monosaccharide (%) | Disacchadde (%) | Others (%) |
| 70 | 0 | | 100 | | | 100 | | | 100 | |
| | 12 | 6.8 | 93.2 C | 0 | 5.9 | 94.1 B | 0 | 5 | 95.0 A | 0 |
| | 24 | 13.9 | 86.1 C | 0 | 12 | 88.0 B | 0 | 8.9 | 90.9 A | 0.2 |
| | 36 | 22 | 77.6 C | 0.4 | 17.8 | 81.9 B | 0.3 | 13 | 87.0 A | 0 |
| | 48 | 30.6 | 68.8 C | 0.6 | 24.6 | 74.9 B | 0.5 | 15.4 | 83.9 A | 0.7 |
| | 60 | 39.6 | 59.6 C | 0.8 | 29.5 | 69.7 B | 0.8 | 17.9 | 81.0 A | 1.1 |
| | 72 | 47.1 | 51.5 C | 1.4 | 33.7 | 65.2 B | 1.1 | 20.2 | 78.3 A | 1.5 |
| 80 | 0 | | 100 | | | 100 | | | 100 | |
| | 12 | 23.8 | 76.2 C | 0 | | | | | | |
| | 24 | 50.7 | 49.3 C | 0 | 36.6 | 63.1 B | 0.3 | 18.9 | 81.1 A | 0 |
| | 36 | 70.3 | 28.7 C | 1 | 45.8 | 52.2 B | 2 | 23.1 | 76.5 A | 0.4 |
| | 48 | 81.8 | 16.5 C | 1.7 | 56 | 41.6 B | 2.4 | 25.3 | 73.4 A | 1.3 |
| | 68 | 86 | 12.1 C | 1.9 | 64 | 33.2 B | 2.8 | 31 | 67.4 A | 1.6 |
| | 72 | 89.5 | 8.2 C | 2.3 | 69.3 | 25.9 B | 4.8 | 35.2 | 62.8 A | 2 |
| 90 | 0 | | 100 | | | 100 | | | 100 | |
| | 12 | 59.4 | 40.4 C | 0.2 | | | | | | |
| | 24 | 94.3 | 4.8 C | 0.9 | 71.1 | 27.8 B | 1.1 | 31.2 | 67.9 A | 0.9 |
| | 36 | 96.9 | 1.2 C | 1.9 | 84.8 | 11.7 B | 3.5 | 43 | 55.9 A | 1.1 |
| | 48 | 95.7 | 0.7 C | 3.6 | 90.3 | 3.6 B | 6.1 | 50.8 | 44.9 A | 4.3 |
| | 80 | 95.4 | 0.6 C | 4 | 91 | 2.6 B | 6.4 | 61.1 | 33.8 A | 5.1 |
| | 72 | 93.9 | 0.5 C | 5.6 | 89.5 | 1.1 B | 9.4 | 68.9 | 24.8 A | 6.3 |
| 95 | 0 | | 100 | | | 100 | | | 100 | |
| | 12 | 73.7 | 25.8 C | 0.5 | | | | | | |
| | 24 | 98.1 | 0.8 C | 1.1 | 89.3 | 4.04 B | 2.7 | 40.1 | 58.0 A | 1.9 |
| | 36 | 97.6 | 0.7 B | 1.7 | 95.4 | 1.1 B | 3.5 | 60.1 | 38.1 A | 1.8 |
| | 48 | 96.4 | 0.6 C | 3 | 95.4 | 1.1 B | 3.5 | 73.8 | 22.0 A | 4.2 |
| | 80 | 95.3 | 0.5 C | 4.2 | 93 | 1.0 B | 6 | 76.8 | 17.0 A | 6.2 |
| | 72 | 92.3 | 0.5 B | 7.2 | 87.8 | 0.9 B | 11. | 79.3 | 12.7 A | 8 |

\* The different characters A, B, and C indicate significant differences (p < 0.05) between Experimental Example 1, Experimental Example 2, and Comparative Example 1 in the horizontal direction.
\* % of monosaccharide and disaccharide indicates a weight ratio (%, w/w), based on the total weight of the analyzed saccharides, and others were classified as other saccharides.

As a result, under the same levels of heat damage (temperature, time), D1 showed a significantly high conversion rate to monosaccharide, followed by D2 and sugar.

Specifically, at 95° C., which is the highest temperature condition, about 74% of D1 was converted to the target ingredient allulose (monosaccharide) after 12 hours, and 98% or more thereof was converted after 24 hours, confirming that allulose was produced. On the contrary, about 58% of D2 was converted after 12 hours, and 89% thereof was converted after 24 hours. 23% and 40% of sugar was converted to monosaccharide, which is relatively insignificant.

Basically, all of Experimental Examples 1 to 2 and Comparative Example 1 showed the same patterns that more disaccharide was decomposed and converted to monosaccharide, as the heating temperature was higher and the heating time was longer. Among them, in Experimental Example 1, the conversion of disaccharide (D1) to monosaccharide (allulose) was significantly fast, and the purity of the converted monosaccharide was maintained at a high level, confirming that the conversion efficiency was high.

In particular, D1, as compared to allulose disaccharide D2, showed the faster allulose conversion and high-purity result.

EXAMPLE 2-2

Utilization of Allulose Precursor in Food Model Including Allulose

Whether the precursor present in the mixture, rather than the precursor alone, is also converted to the target ingredient was examined by adding disaccharide D1 to a food model including allulose as a main ingredient.

In detail, drink models were prepared by dissolving pure allulose crystals with minimum impurities (CJ Cheiljedang, purity of 99.8% or more) and D1 among the previously isolated disaccharides in purified water (Experimental Example 3). The prepared Experimental Example 3 was heat-treated for about 1 hour at 95° C., which is one of the common beverage processing conditions. Whether the disaccharide added to Experimental Example 3 was converted to allulose before and after heat treatment was examined by HPLC under conditions of Table 1. The detailed composition ratio of each sample and changes before and after heating are shown in Table 4 below. Likewise, all experiments were performed in triplicate.

TABLE 4

| Section | Heating time (95° C.) | Weight ratio, based on total solid content (%) | | | Total solid content (g/100 g) |
|---|---|---|---|---|---|
| | | Monosaccharide (Allulose) | Disaccharide (D1) | Others | |
| Experimental Example 3 | Initial | 95.24 | 4.74 | 0.02 | 10.0 |
| | After 60 minutes | 98.46 | 1.53 | 0.01 | 10.0 |

As a result, Experimental Example 3, in which D1 as the allulose precursor was added to allulose, showed that D1 was converted to the target ingredient allulose, and the purity of allulose was increased. Specifically, Experimental Example 3 showed that D1 included at a ratio of about 4.7% based on the total solid content was decreased to a ratio of about 1.5% (−3.2%) after heat treatment, whereas the target ingredient allulose was increased in the corresponding amount.

In other words, D1 was converted to the target ingredient allulose under general processing (heating) conditions, and at the same time, unintentional products were not produced, indicating that D1 has suitable properties as the precursor.

Furthermore, since D1 as the precursor receives thermal energy, a positive effect of suppressing denaturation (loss) of the useful component allulose due to exposure to excessive thermal damage may be expected.

EXAMPLE 2-3

Comparison of Precursor Utilization According to Temperature and Solid Concentration Conditions The conversion characteristics of D1 to allulose were examined under various conditions of temperature and solid concentration. The isolated precursor D1 was added to pure allulose monosaccharide in the same manner as in Example 2-2, previously tested, and the concentration of solids was adjusted using purified water. Detailed compositions of the prepared Experimental Examples 4 to 6 are shown in Tables 5 and 6 below.

First, the conversion rates of D1 were compared, when heated for 24 hours by varying the temperature condition at 40° C. 60° C., and 80° C. (Table 5).

TABLE 5

| Sample | Section | Heating temperature (° C.) | Heating time (hr) | Weight ratio, based on Total solid content (%) | | Total solid content (9/100 g) |
|---|---|---|---|---|---|---|
| | | | | Monosaccharide (Allulose) | Disaccharide (D1) | |
| Experimental Example 4 | Initial | — | — | 94.3 | 2.0 | 20.0 |
| | After heating | 40 | 24 | 95.1 B | 1.5 A | 20.0 |
| | | 60 | 24 | 97.6 A | 0.6 B | 20.0 |
| | | 80 | 24 | 96.5 C | 0.5 C | 20.0 |

* The different characters A, B, and C in the vertical direction indicate significant differences ($p < 0.05$), as compared to initial preparation of the same sample.

As in the previous experiment, it was confirmed that D1 was converted to the desired ingredient allulose under all temperature conditions, and the purity of allulose was increased. In particular, it was confirmed that D1 was almost converted to allulose when heated at 60° C. to 80° C.

Next, the conversion rates of C1 were compared when heated at a high temperature (121° C.) for a short period of time (15 minutes) by varying the solid concentration at 10% and 30% (w/w, g/100 g) (Table 6).

was increased. In particular, it was confirmed that as the total solid content became lower, the conversion efficiency of D1 to allulose was relatively high even after heat treatment.

Through these experimental processes, it was confirmed that the allulose disaccharide of the present disclosure has high efficiency as a precursor to be converted to allulose, which is a high-value-added material beneficial to consumers.

In particular, it was confirmed that the final target material, allulose was generated through a simple heating reaction (normal processing level) rather than a complicated conversion reaction, and it has the potential to prevent allulose from being exposed to excessive heat damage without the presence of unintentional impurities. Based on this effect, it is expected that D1 may be utilized as a precursor capable of enhancing and preserving the purity of allulose in food and beverage products.

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds, are therefore intended to be embraced by the claims.

Effect of the Invention

An allulose precursor of the present disclosure may be simply converted to allulose, and the level of conversion to

TABLE 6

| Sample | Section | Total solid (9/100 g) content | Weight ratio, based on total solid content (%) | | Heating temperature (° C.) | Heating time (hr) |
|---|---|---|---|---|---|---|
| | | | Monosaccharide (Allulose) | Disaccharide (D1) | | |
| Experimental Example 5 | Initial | 10.0 | 95.2 | 2.1 | — | — |
| | After heating | 10.0 | 98.6 A | 0.5 B | 121 | 15 |
| Experimental Example 6 | Initial | 30.0 | 95.2 | 2.1 | — | — |
| | After heating | 30.0 | 97.3 B | 0.8 A | 121 | 15 |

* The different characters A, B, and C in the vertical direction indicate significant differences ($p < 0.05$), as compared to initial preparation of the same sample.

As in the previous experiment, it was confirmed that D1 was converted to the desired ingredient allulose when heated under all concentration conditions, and the purity of allulose substances other than allulose is low. Thus, the allulose precursor may be usefully applied to improve the quality stability of food compositions including allulose.

What is claimed is:

1. A method of preparing allulose, the method comprising heating a composition including an allulose disaccharide, wherein the allulose disaccharide has two allulose molecules linked by a glycosidic bond, the glycosidic bond linking a hydroxyl group at C2 position of one allulose molecule of the two allulose molecules to a hydroxyl group at any one position of C1 to C6 positions of the other allulose molecule.

2. The method of claim 1, wherein the allulose disaccharide is represented by Formula 1 below:

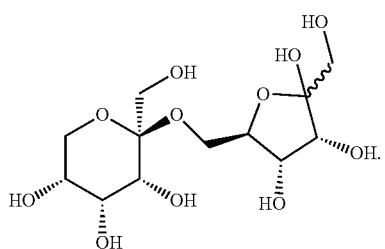

[Formula 1]

3. The method of claim 1, wherein the heating is performed at a temperature of 60° C. or higher and 100° C. or lower.

4. The method of claim 1, wherein the composition including the allulose disaccharide further includes allulose.

5. The method of claim 1, wherein the allulose disaccharide included in the composition is an allulose precursor.

6. The method of claim 1, wherein the allulose disaccharide is represented by Formula 2 or 3 below:

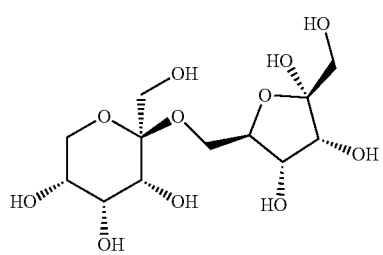

[Formula 2]

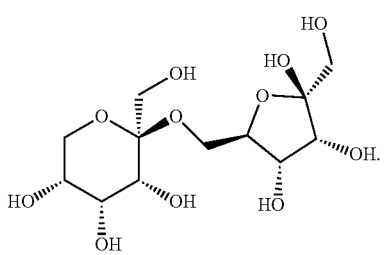

[Formula 3]

* * * * *